(12) United States Patent
Mather et al.

(10) Patent No.: US 8,431,151 B2
(45) Date of Patent: Apr. 30, 2013

(54) ANTIMICROBIAL NANOSTRUCTURED HYDROGEL WEB CONTAINING SILVER

(75) Inventors: Patrick Mather, Manlius, NY (US); Jian Wu, Pittsburgh, PA (US); Dacheng Ren, Syracuse, NY (US); Shuyu Hou, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 247 days.

(21) Appl. No.: 12/851,932

(22) Filed: Aug. 6, 2010

(65) Prior Publication Data

US 2011/0033520 A1    Feb. 10, 2011

Related U.S. Application Data

(60) Provisional application No. 61/231,844, filed on Aug. 6, 2009.

(51) Int. Cl.
*A61L 15/00* (2006.01)
*A61K 9/14* (2006.01)
*A61K 33/38* (2006.01)

(52) U.S. Cl.
USPC ............ 424/445; 424/486; 424/618

(58) Field of Classification Search .............. None
See application file for complete search history.

(56) References Cited

U.S. PATENT DOCUMENTS

| 7,091,297 B2 * | 8/2006 | Mather et al. ............ 528/28 |
| 2005/0266081 A1 * | 12/2005 | Rogozinski ............ 424/484 |
| 2006/0167190 A1 * | 7/2006 | Trabesinger et al. ...... 525/457 |
| 2007/0134307 A1 * | 6/2007 | Xiao et al. ............. 424/447 |

OTHER PUBLICATIONS

Wu et al., Mater. Res. Soc. Symp. Proc., 2008, vol. 1060, pp. LL03-LL10.*

* cited by examiner

*Primary Examiner* — Brian Gulledge
(74) *Attorney, Agent, or Firm* — David L. Nocilly; Bond Schoeneck & King

(57) ABSTRACT

Robust polymeric hydrogels and a method to fabricate antimicrobial non-woven fibrous wound dressing with controlled silver release that may be used for anti-infective medical implants and anti-infective coating for implantable medical device. The hydrogels may be provided in non-woven fibrous wound dressing and anti-infective implantable medical devices, especially for reconstructive oral and bone surgery.

20 Claims, 9 Drawing Sheets

ANTIMICROBIAL NANOSTRUCTURED HYDROGEL WEB CONTAINING SILVER

CROSS-REFERENCE TO RELATED APPLICATIONS

This application claims priority to U.S. Provisional Patent Application Ser. No. 61/231,844 filed Aug. 6, 2009, which is hereby incorporated by reference in its entirety.

BACKGROUND OF THE INVENTION

1. Field of the Invention

The present invention relates to hydrogels and, more specifically, to hydrogel webs containing silver compounds.

2. Description of the Related Art

Treatment of nosocomial infections costs 11 billion dollars every year in the U.S. alone. About half of these infections are related to medical devices that are implanted in patients for different lengths of duration. It is well documented that the microbes causing device-related infections are attached to surfaces and grow into biofilms, which are highly hydrated structures comprised of a polysaccharide matrix secreted by the bound microbes. Biofilm cells are up to 1000 times more tolerant to antimicrobial agents (hereafter, antimicrobials) and disinfectants than their free-swimming counterparts. Because antibiotics can only eliminate planktonic cells, biofilm-associated infections are normally persistent and associated symptoms reoccur upon the release of cells from biofilms. Clinical cure of device-associated infections requires total removal of the device followed by prolonged antibiotic therapy to effectively clear the infection. With the serious medical consequences of device-associated infections and significant difficulties in treating established biofilms, effective methods for preventing biofilm formation are necessary. Conceptually, the prevention of biofilm formation could be achieved either by covalently modifying the surface with antimicrobials or controlled release of antimicrobials from the surface. Because increasing evidence has shown that medical devices are quickly covered by host proteins once implanted in a human body, materials capable of controlled and sustained release of antimicrobials are highly desired.

Silver, being an antimicrobial agent, has a history in wound healing dating at least two thousand years—since ancient Greece and Rome, owing to its low toxicity to human cells. For example, 16 bacterial species tested, including *Escherichia coli, Pseudomonas aeruginosa*, and *Staphylococcus aureus* are inhibited at 1.25 µg/mL silver ($Ag^+$), while 4 µg/mL silver ($Ag^+$) does not exhibit any obvious detrimental effects to mouse bone marrow cells (as a susceptible normal mammalian system). Although modern antimicrobial quickly developed in the last century following the introduction of sulphonamides and penicillin, silver compounds have continued to be attractive as antimicrobial agents due to their unique advantages: (1) a broad spectrum antimicrobial properties against both gram-positive and gram-negative bacteria and (2) existence of multiple cellular targets and therefore less chance for development of resistance in bacteria. For example, silver sulfadiazine (SSD), an antimicrobial agent containing silver nitrate ($AgNO_3$) and a sulphonamide antibiotic, was introduced in 1968. Due to its controllable delivery of silver ions to infected wounds, it has been widely applied to treat infections in burns and scalds. It is believed that the ionic silver ($Ag^+$) released from the dressing has high activity to bind to intracellular proteins and nucleic acids of bacteria, leading to structural changes in bacterial cell membranes. These effects further result in the cellular distortion and loss of viability of the organism. In addition, $Ag^+$ can interact with and denature DNA and RNA, thereby inhibiting cell division and replication. More recently, a variety of silver-based products have been commercialized varying from wound dressing to vascular and urinary catheters. The carrier materials used for silver loading vary from alginates (i.e., Acticoat™, Smith and Nephew and Silvercel, Johnson & Johnson), to hydrogel (i.e., Silvasorb™, Medline), hydrocolloid (i.e., Contreet HTM, Coloplast) and foam (i.e., Contreet FTM, Coloplast). This variety in material form provides wide options in clinical therapy. Recently, the new absorbent non-woven "hydrofiber" dressing, Aquecel Ag™ (Conva Tech), has been introduced. Such non-woven hydrofibers, consisting of sodium carboxymethylcellulose, show apparent advantages of fluid-handling capacity and ease of application and removal.

BRIEF SUMMARY OF THE INVENTION

In accordance with the foregoing objects and advantages, the present invention provides robust polymeric hydrogels as well as a method to fabricate antimicrobial non-woven fibrous wound dressing with controlled silver release. The present invention also provides a potential material and fabrication solution for anti-infective medical implants and anti-infective coating for implantable medical devices. The present invention includes significantly prolonged antimicrobial effects that reduce nursing costs, improves fluid-handling capacity and ease of application and removal relieve patients' pain, avoids "lateral wicking", and consequently prevents associated excoriation and maceration of the skin at the edge of heavily exuding wounds, by reducing swelling, and provides for facile tailoring of the overall hydrogel properties and the resulting antimicrobial activity. The present invention may be provided in non-woven fibrous wound dressing and anti-infective implantable medical devices, especially for reconstructive oral and bone surgery.

In the present invention, a nanofiber web is used as the delivery vehicle for silver ions. To fabricate non-woven fibrous scaffolds, researchers have turned to the electro-spinning technique as the most extensive preparation method in the last decade. Electrospun fibers can be prepared to feature fiber diameters that range from several micrometers down to tens of nanometers, simply by tuning the experimental conditions. Also, the materials used to generate electrospun fibrous scaffold are diverse, ranging from polymers, polymer blends, and composites with other materials and additives, such as growth factors, enzymes, other cell-regulatory biomolecules, among others. Recently, several research groups have succeeded in preparing electro-spun polymeric fibrous scaffolds incorporating $AgNO_3$ and Ag nano-particles for microbiocidal applications. These studies revealed antimicrobial effects of the fibrous scaffolds containing Ag; however, they did not demonstrate prolonged efficacy. The inventors have successfully prepared PEG-based multi-block thermoplastic polyurethanes incorporating polyhedral oligomeric silsesquioxane ("POSS"). The resulting organic-inorganic hybrid hydrogels, being good candidates for biomedical applications, exhibited excellent mechanical properties and tunable swelling behavior. The preparation and characterization of POSS-PEG hybrid thermoplastic polyurethanes (TPUs) and their nano-structured electrospun fibrous hydrogel scaffolds incorporating $AgNO_3$ are the subject of the present invention, which includes a surprising ability of the electrospun hydrogel webs to regulate biofilm control in a sustained manner over time.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 6:
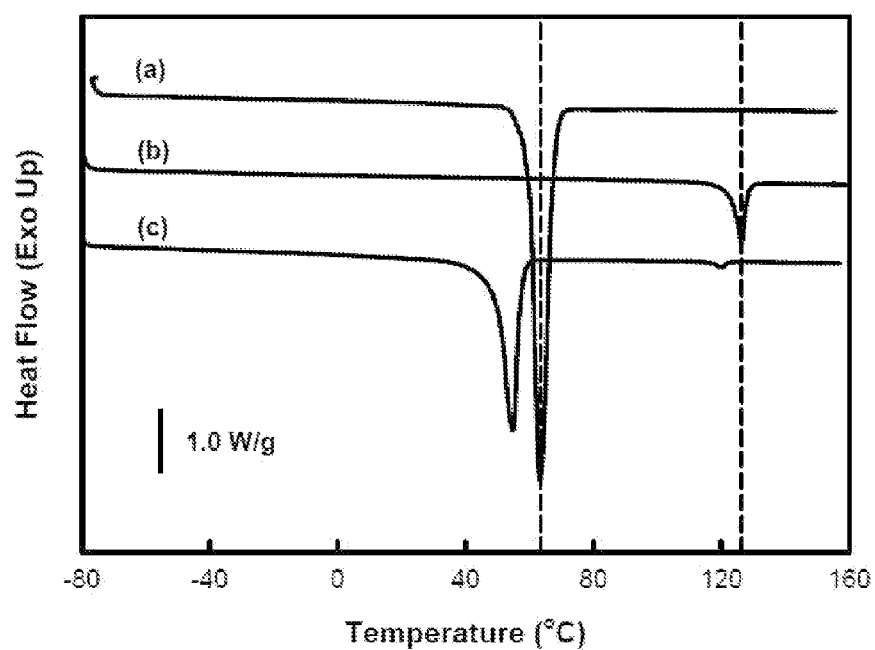
Figure 7:
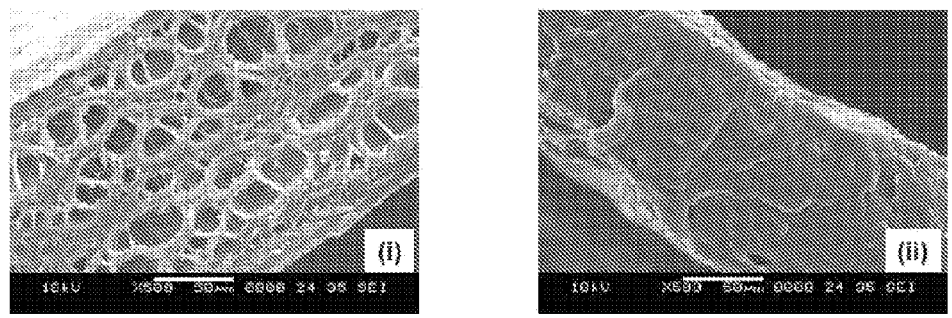
Figure 8:
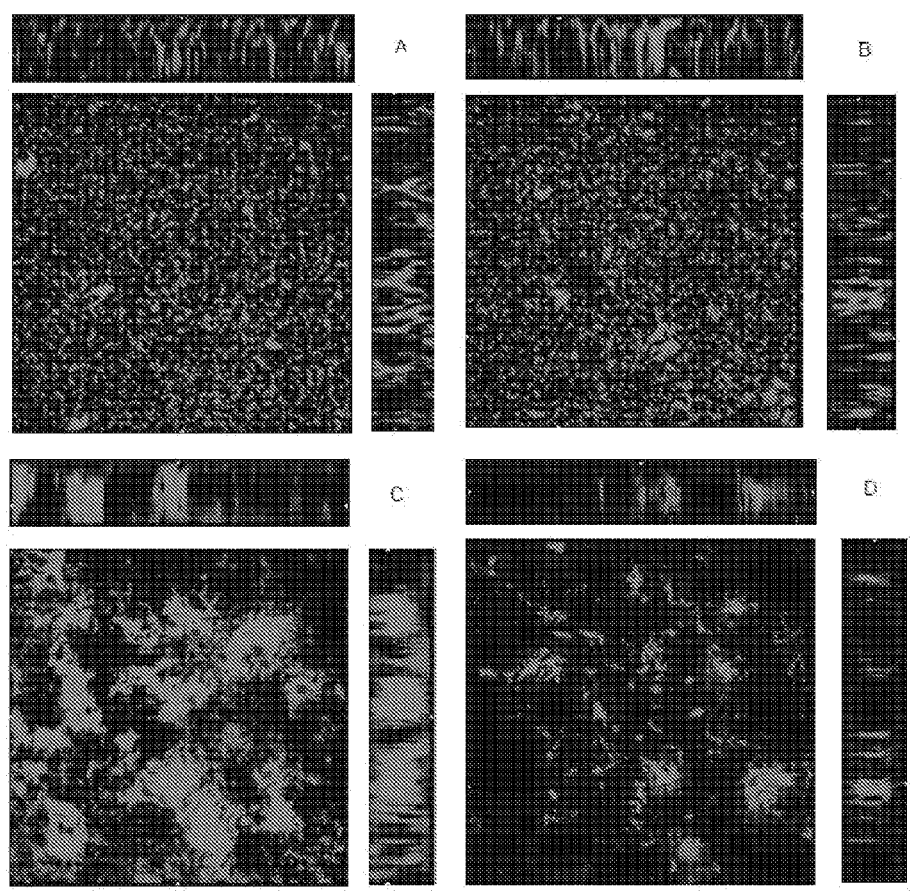

FIG. 6 is a graph of the differential scanning calorimetry (DSC) analysis of the thermal plastic polyurethanes (TPUs) from PEG and TMP POSS-diol macromers: (a) PEG homopolymer, 10 kg/mol, (b) pure POSS-diol, (c) TPUs prepared from PEG homopolymer (10 kg/mol) and POSS-diol with feeding molar ratio=2:1. The DSC trace curves recorded the second heating with ramping rate of 10° C./min. The dash lines were referred for melting temperatures of pure PEG and POSS-diol;

FIG. 7 is a series of micrographs of internal microstructures of frees-dried hydrogels prepared from (i) cast film and (ii) electro-spun nano-fibrous mat with 1 wt-% $AgNO_3$; and FIG. 8 is a series of cut views of 14-day *E. coli* biofilms formed on casting films: (A) without silver; or (B) with silver and nanofiber webs; (C) without silver; or (D) with silver.

DETAILED DESCRIPTION OF THE INVENTION

Referring now to the drawings, wherein like reference numerals refer to like parts throughout, the present invention comprises robust polymeric hydrogels as well as a method to fabricate antimicrobial non-woven fibrous wound dressing with controlled silver release, prepared as described below.

Sample Preparation

Thermoplastic polyurethanes (TPUs) were synthesized to contain soft segments, consisting of polyethylene glycol (PEG, 10 kg/mol), alternating with hard segments consisting of isobutyl ($^i$Bu) functionalized POSS diol (hereafter "POSS diol") and lysine methyl-ester diisocyanate (LDI), as shown in FIG. 1. A one-step method was used to synthesize the TPUs. First, PEG (10 kg/mol, Fluka, Inc.) was purified by preparing a THF solution, precipitating it into n-hexane several times, and filtering the resulting powder. These steps were repeated several times. The purified powder was then dried in a vacuum oven at room temperature overnight. LDI (Kyowa Hakko Chemical Co., Ltd.) was purified by vacuum distillation at an oil bath temperature of 180° C. 2,2,4-trimethyl-1,3-pentane (TMP) POSS diol (R-group=$^i$Bu), hereafter "POSS diol" (95%, Hybrid Plastics) was used without further purification. In a 100 ml three-neck flask, 1.052 g of POSS-diol (1.0 mmol) and 5.0 g of PEG (0.50 mmol) were dissolved in toluene (Fisher, ACS Certified), which had been dried with the aid of calcium hydride ($CaH_2$, Aldrich). Under the protection of a nitrogen purge, the flask was heated to 50° C., and a stoichiometric amount of LDI (0.275 ml; $\rho$=1.157 g/mL; 1.5 mmol) was added into the 10 wt-% toluene solution. The reaction mixture was further heated to 90° C. and several drops of dibutyltin dilaurate catalyst were added through a syringe. The reaction was kept at 90° C. for 5 hours under the nitrogen purge and a distinctive viscosity rise was observed. The polymer solution was then precipitated into an excess of n-hexane (a good solvent for the removal of unreacted POSS), filtered, and washed with de-ionized water several times in order to remove any unreacted PEG.

TPU samples were dissolved into DMF to a concentration of 20% (wt/vol) for electro-spinning processing. To prepare antimicrobial fibrous scaffolds, $AgNO_3$ was incorporated into the DMF solutions at a level of 1.0 wt-% relative to the polymer mass. For comparison, we also prepared cast films by pouring 5% (wt/vol) polymer/DMF solutions (with and without 1-wt % $AgNO_3$) into casting dishes, following which the solvent was evaporated to yield semi-transparent, mechanically robust films with the thicknesses of about 200 µm, comparable to the electrospun fibrous scaffolds.

Polymer Characterization

The molecular weight and molecular weight distribution of the polymers used for electrospinning were determined by gel permeation chromatography (GPC) (Waters 2414) equipped with multiangle laser light scattering (Wyatt miniDAWN) using three angles (45°, 90°, 135°) to determine the absolute molecular weight. The samples, dissolved in THF at a concentration of approximately 0.2 wt %, were filtered and injected at 35° C. using THF as eluent and at a flow rate of 1 mL/min. The actual ratio of POSS to PEG in the product was determined by $^1$H-NMR spectra employing a Bruker DPX-300 high resolution spectrometer in $CDCl_3$ using methods described in prior work, and described further below.

The melting behaviors of the POSS hard-block and PEG soft-block in the thermoplastic hybrid polyurethanes were investigated by DSC (TA Instruments Q200) equipped with a mechanical intercooler under a continuous nitrogen purge (50 mL/min) by the following procedure. Before DSC analysis, both cast films and electro-spun fibrous webs were dried at a vacuum oven at room temperature for several days. After annealing each sample at 155° C. for 5 min to melt residual POSS crystals, the samples (5~10 mg) were cooled to −50° C. with a ramping rate of −10° C./min, and then heated up to 155° C. with a ramping rate of 10° C./min. During this second heating run, we observed the latent heat for the melting transitions of both the POSS hard segment and PEO soft segment of the hydrogel-forming TPU.

Nanofiber Processing by Electrospinning

Nanoscale fibrous mats containing $AgNO_3$ were prepared by an electrospinning technique. Our electro-spinning set-up consisted of a syringe pump (KD Scientific, Inc.) that delivered polymer solution (20% wt/vol) at a flow rate of 0.1 mL/h through a stainless steel needle (inner diameter (ID)=0.3 mm) charged to a high positive potential of 12 kV relative to an adjacent grounded steel drum (radius=51 mm) rotating at 400 rpm with the axis of rotation oriented perpendicular to the syringe needle. The needle tip was pointed at the drum axis of rotation and was separated from the drum surface by 5 cm, yielding an apparent field strength of 2.4 kV/cm. The resulting electro-spun fibers were collected on the rotating drum and had the appearance of a white, non-woven fabric. The thickness was approximately 200 μm (though compressible) for an electrospinning time of 12 h. All of the collected samples were dried under vacuum at room temperature for several days, removing all residual solvent.

Swelling Behavior

After measuring their lengths and weights, dry cast films and electro-spun fibrous mats were immersed into Millipore water for 24 h at room temperature in order for them to reach states of equilibrium swelling. Before measuring the lengths and weights of the hydrated samples, the excess water on their surface were removed by blotting with filter paper. The water uptake content was calculated as follows: Water Uptake, WU (%)=$(m_w-m_d)/m_d \times 100\%$, where mw and are the masses of dried and swollen samples, respectively. The swelling ratio was calculated by: Swelling Ratio, SR (%)=$-(1_w-1_d)/1_d \times 100\%$, where $1_w$ and $1_d$ are the lateral dimensions of dried and swollen samples, respectively.

Electron Microscopy

The morphologies of the electrospun TPU fibrous scaffolds were investigated using scanning electron microscopy (SEM; JEOL, JSM-5600). The *Escherichia coli* biofilms formed on these scaffolds were also analyzed by SEM. Since the PEG-POSS TPUs can be swollen in ethanol and isopropanol, the conventional experimental protocol to fix the *E. coli* morphology is not suitable in our current case. Here, we have to choose the alternative as following. Before SEM analysis, the scaffolds infiltrated with *E. coli* biofilms (see directly below) were gently washed three times by dipping them vertically in 0.85% (wt./vol.) NaCl buffer (clean buffer was used for each dipping procedure), drying at ambient condition for one week, and finally drying in a vacuum oven at room temperature for three days. All of the samples were coated with gold for 60 s using an Enton Vacuum-Desk II gold sputter coater to yield coating thickness of approximately 200 Å, suitable for SEM observation without charge accumulation.

Bacterial Strains and Growth Media

To study the antimicrobial properties of nanostructured hydrogel webs containing silver, *E. coli* K12 strain RP437 was used. To visualize the biofilms with fluorescence microscopy, *E. coli* RP437 was labeled with constitutively expressed DsRed-Express fluorescent protein by transformation of plasmid pRSH103. In particular, pRSH103 was derived from the prokaryotic expression vector pDsRed-Express (BD, Franklin Lakes, N.J.) by replacing the ampicillin-resistant marker with the tetracycline (Tet) resistant marker $tet^R$. *E. coli* RP437/pRSH103 was grown in Luria-Bertani (LB) medium containing 10 g/L tryptone, 5 g/L yeast extract, and 10 g/L sodium chloride. Tet was added to all growth media at a concentration of 10 μg/mL to maintain the plasmid. To test for the formation of biofilms, an overnight culture of *E. coli* RP437/pRSH103 was grown with shaking at 200 rpm (Orbit Shaker Model 3520, Lab-Line Instrument, Inc, Melrose Park, Ill.) in LB medium supplemented with 10 μg/mL Tet at 37° C. The overnight culture was used to inoculate biofilm cultures in the same medium to an optical density at 600 nm ($OD_{600}$) of 0.05 as measured with a Genesis 5 spectrophotometer (Spectronic Instruments, Rochester, N.Y.).

UV Sterilization

To sterilize the nanostructured hydrogel samples with and without $AgNO_3$, UV illumination under a universal UV light source (G36T5L/C, 254 nm, 42 W, NuAire Inc, Plymouth, Minn.) in a Biological Safety Cabinet (Model NU-425-600, Class II, Type A/B3, NuAire Inc, Plymouth, Minn.) was used. To test the efficacy of UV sterilization, the nanofibrous webs were UV-illuminated for 5, 10, 15, 20, 25, or 30 min for each side of the specimens, followed by the transfer of each web sample into sterile polystyrene test tubes (17×100 mm, Evergreen Scientific, Los Angeles, Calif.) containing 5 mL sterile LB medium. The tubes containing the nanofibrous webs were incubated with shaking at 200 rpm at 37° C. overnight. The $OD_{600}$ was measured to determine the efficiency of UV sterilization. In addition, colony forming units (CFU) were also counted to confirm the results. The minimum UV illumination time with no bacterial growth was used for sterilizing all the nanofibrous webs for biofilm study.

Long-term Biofilm Formation Assay

To evaluate the antimicrobial activities of the hydrogel mats, the biofilms of *E. coli* RP437/pRSH103 on the control (no $AgNO_3$) and $Ag^+$-releasing webs (containing $AgNO_3$) were monitored for 2 wk. To grow biofilms, the *E. coli* RP437/pRSH103 cells of an overnight culture were washed with 0.85% NaCl buffer twice and then resuspended in LB medium supplemented with 10 μg/mL Tet to an $OD_{600}$ of 0.05. Both the control (no $AgNO_3$) and $Ag^+$-releasing mats (containing $AgNO_3$) were cut into 1×2 cm pieces, sterilized by UV illumination as described above, soaked in sterile Millipore water supplemented with 10 μg/mL Tet for 1 h, and finally washed twice with the same solution to remove any soluble chemicals in the webs. The nanofibrous webs were then transferred to petri dishes containing *E. coli* RP437/pRSH103 and growth medium as described above ($OD_{600}$=0.05). The 8 biofilm cultures were incubated in the dark at 37° C. for 2 wk. To provide nutrients for biofilm development, the nanofibrous mats were transferred to fresh medium every day and the inoculation $OD_{600}$ was adjusted to 0.05 (by inoculation from an overnight culture) upon transfer. Two control webs and two $Ag^+$-containing webs were examined with fluorescence microscopy to reveal and quantify any biofilm formation at 1, 6, 10, and 14 d after inoculation using an Axio Imager M1 fluorescence microscope (Carl Zeiss MicroImaging GmbH, Gottingen, Germany). To determine if there is a difference in antimicrobial activities between the $Ag^+$-containing webs and cast films of the same composition, the control films (no silver) and silver films were also studied in a long-term experiment using the same method for the $Ag^+$-containing nanofibrous webs, described above.

Microscopy Assay and Image Analysis

*E. coli* biofilms were imaged using fluorescence microscopy with z-axis (thickness) optical sectioning. For this purpose, each sample was first washed gently as described above for SEM analysis. The *E. coli* biofilm cells that express DsRed-Express constitutively were visualized by excitation with a mercury vapor shot-arc lamp (HBO 103 W/2, OSRAM GmbH, Augsburg, Germany) at 558 nm. The resulting fluorescence emission was detected at 583 nm. The nanofibrous webs or cast films were gently put on a microscope slide (25 mm×75 mm×1 mm, Fisher Scientific, Pittsburgh, Pa.) and covered with a microscope cover slide (24 mm×60 mm, VWR International, LLC, West Chester, Pa.). A series of vertically staggered (z-sectioned) images (normally 30 images) were obtained with 2 μm spacing, allowing for a three dimensional view of the biofilm. At least five spots were randomly selected and examined for each web or film sample with a total of 150 images analyzed to calculate measures of biofilm formation. Specifically, the surface coverage (%), thickness (μm), and biomass (volume/area, $\mu m^3/\mu m^2$) were calculated using the COMSTAT software written on the Matlab platform.

PEG-Based Multiblock Thermoplastic Polyurethanes Incorporated by POSS Moieties.

Figure 1A:
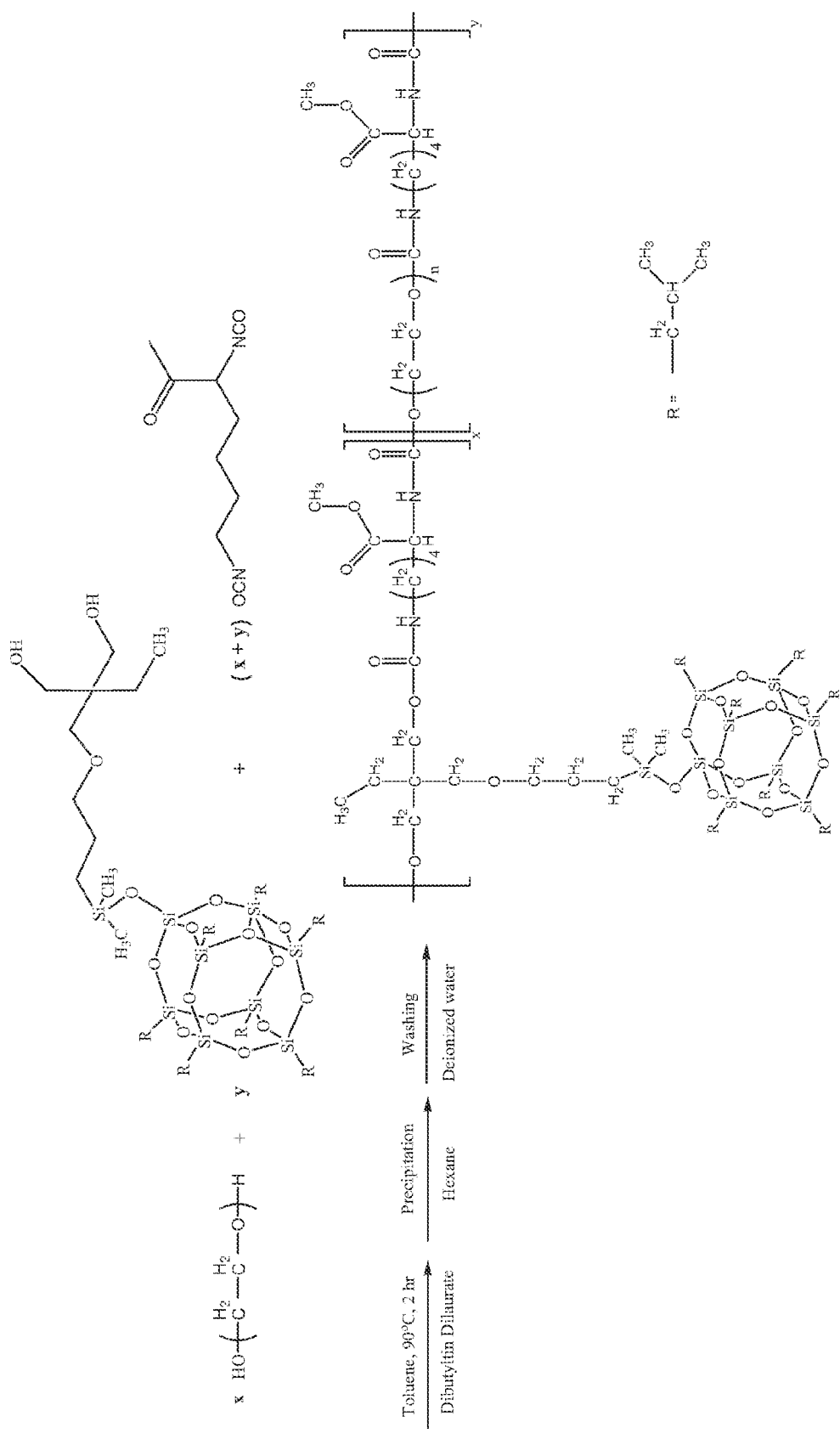
FIG. 1A is a diagram of the synthesis of PEG-based multiple-block thermoplastic polyurethane incorporated by POSS macromer.

As the delivery vehicle for silver ions, we have synthesized polyurethanes utilizing Poly(ethylene glycol) (PEG, the dihydroxyl-terminated version of PEO), as the soft block. PEG is one of the most widely investigated polymers for medical applications, due to its very low toxicity, high biocompatibility and high hydrophilicity. As an example, PEG-based cross-linked networks can be designed to form hydrogels with tailored properties based on crosslinking density. Usually, PEG-based hydrogels are obtained through polymerization of acrylate or methacrylate end-capped PEGs. To meet the electrospinning requirements of solubility and viscosity, PEG was physically crosslinked by introducing hydrophobic moieties along the backbone of linear (not crosslinked) chains—an approach amenable to the processing of fibrous webs. In particular, PEG-based multi-block thermoplastic polyurethanes were prepared by incorporating hydrophobic polyhedral oligosilsesquioxane (POSS) moieties in an alternating fashion (FIG. 1A). Such covalent incorporation of hydrophobic moieties has been verified to induce micro-phase separation with hydrophilic PEG in thermoplastic polyurethanes (TPUs) with the linkage of 4,4-methylenebis(phenyl-isocyanate) (MDI). For the present work, the non-aromatic lysine methyl-ester diisocyanate (LDI) was selected in place of MDI for urethane polymerization of PEG and POSS in a TPU format.

GPC analysis revealed that the molecular weight of the resultant TPU was approximately n M=104 kg/mol, with a polydispersity of 1.11. This moderately high molecular weight proved to allow fiber formation by electrospinning at low enough concentrations to allow for submicron diameters as described below. $^1$H-NMR analysis was used to quantitatively determine the molar ratio of POSS to PEG by comparing ratio of the integration value of proton signal at d 0.12 ppm (—O—Si(CH$_3$)$_2$—CH$_2$—) for POSS macromers to the integration value of proton signal at d 3.64 ppm (PEG, —CH$_2$—CH$_2$—O—). Before comparison, both of the integration values were normalized to those for a single 10 proton. We found the actual molar ratio (1.3:1) of POSS and PEG10k was smaller than the feeding ratio (2.0:1), a finding that we ascribe the steric effect of the large POSS macromer. DSC analysis revealed the existence of two distinct melting peaks, which are centered at 51.7° C. and 114° C., respectively (FIG. 7 and Table 1).

TABLE 1

Thermal Analysis of POSS-PEG TPUs

| POSS/PEG10k (Feed Ratio) | PEG, wt % (Actual) | $T_g$ (° C.) | $T_m^{PEG}$ (° C.) | $\Delta H^{PEG}$ (J/g) | $T_m^{POSS}$ (° C.) | $\Delta H^{POSS}$ (J/g) |
|---|---|---|---|---|---|---|
| 2/1 | 84.17 | −48.4 | 54.7 | 105.2 | 120.1 | 2.04 |

By comparison with the melting points of pure PEG ($T_m$=63.2° C.) and POSS macromer ($T_m$=126.3° C.), we can ascribe the low melting peak to PEG-rich domain and the high one to POSS-rich phase, although both of them are lower than their pure counterparts. The existence of two distinct melting events indicates the formation of PEG-rich and POSS-rich micro-phases. As mentioned in our previous research work, such a micro-phase separation is driven by the thermodynamic immiscibility between hydrophilic PEG and hydrophobic POSS moieties and allows hydrogel formation upon contact with water.

Electrospinning of POSS-PEG TPUs

Figure 1B:
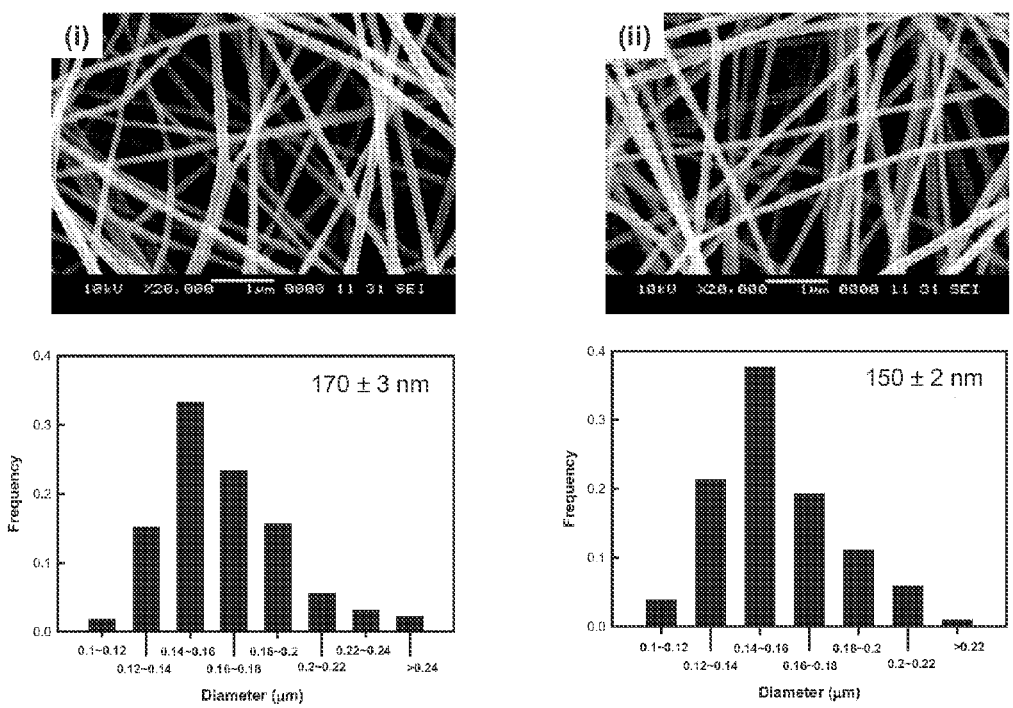
FIG. 1B is a series of SEM micrographs and a histogram of fiber diameter distribution of electrospun fibrous scaffolds of TPUs made from: (i) 20-% DMF without $AgNO_3$ and (ii) 20 wt-% DMF with 1-wt % $AgNO_3$; where the inset numbers represent average diameter of fibrous scaffolds (95% confidence interval)

The electro-spinning of polymer solutions containing AgNO$_3$ has been previously reported. In order to homogeneously disperse AgNO$_3$ in such solutions, water is most often selected as the solvent or as one component part of mixed a solvent system. However, Ag$^+$ in aqueous polymer solutions is subject to electrochemical reduction to metallic Ag and/or AgO$_2$ if the needle is made of steel or copper. These by-products will effectively block the electro-spinning needle. In order to avoid this problem, we chose DMF, a good solvent to both POSS-PEG TPUs and AgNO$_3$, as the electro-spinning medium. During the electro-spinning process, we did not observe any blocking phenomenon. We postulate that in this system AgNO$_3$ is coordinated with DMF and unable to release free Ag$^+$ into solution by ionization, resulting in reduction inhibition. The morphology of electro-spun fibrous mats of the POSS-PEG TPU was characterized by SEM, and representative micrographs are shown in FIG. 1B. The fiber diameter and diameter distribution were determined by analysis of SEM micrographs (20,000×), revealing that the fiber diameters for both samples range from 100 nm to 250 nm, specifically 170±3 nm (95% confidence interval) for the electro-spun fibers without AgNO$_3$ incorporation and a slightly smaller 150±2 nm 11 (95% confidence interval) for those with 1.0 wt -% AgNO$_3$ incorporation. The slight decrease in fiber diameter upon addition of silver nitrate can be ascribed to an increased electrical conductivity of the electro-spinning polymer solution, a finding previously reported for other electrospinning systems.

Swelling Behavior

Figure 2:
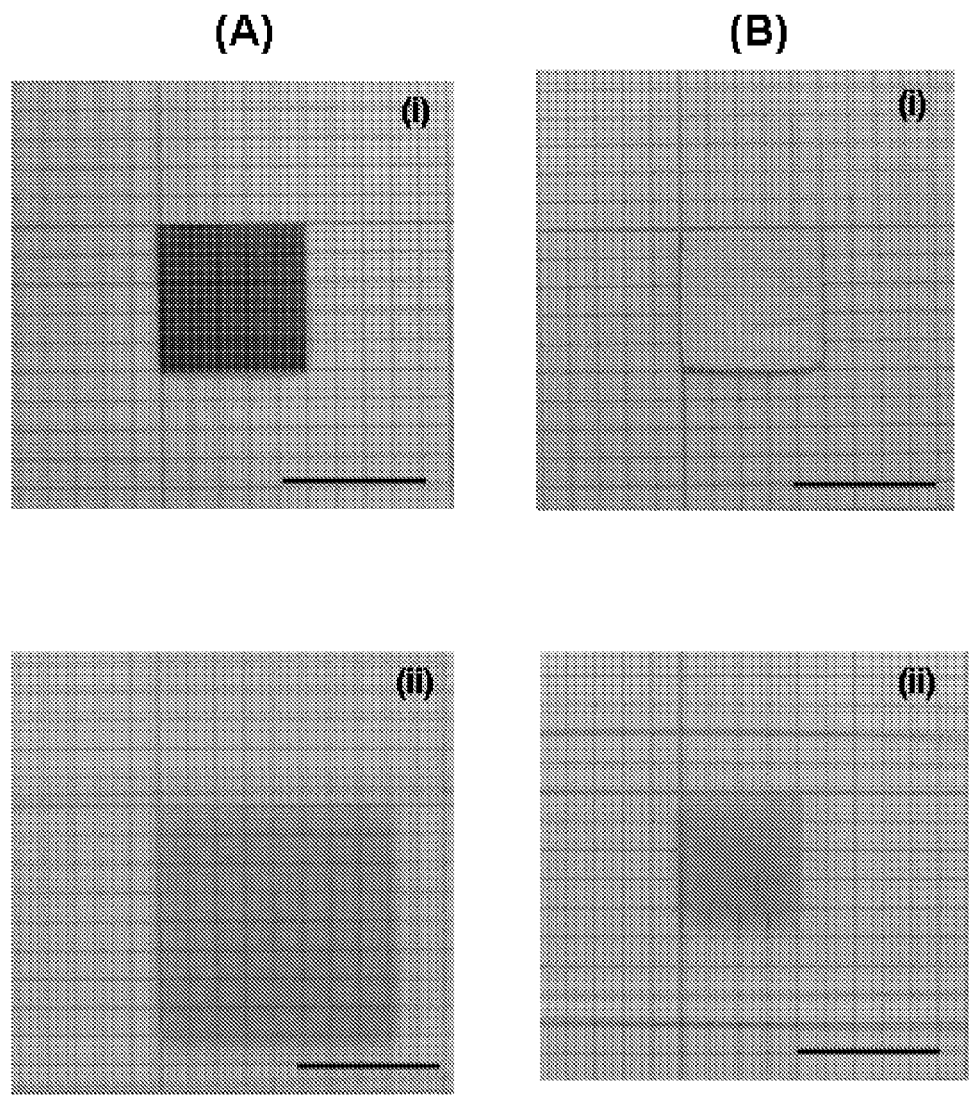
FIG. 2 is a series of digital images of POSS-PEG TPUs with 1.0 wt-% $AgNO_3$ loading: (A) cast film and (B) espun fibrous mat from 20 wt-% DMF, varying with (i) before and (ii) after hydration; where the scale bar is 1 cm.

A study of the antimicrobial behavior of silver-containing nanofibrous webs necessarily involves their contact with water. As such, the water-swelling behavior of the nanofibrous webs relative to conventional film forms of the same materials is of primary importance. In principle, the swelling extent of hydrogels is determined by a balance between the driving force of an exothermic mixing enthalpy ($\Delta H_{swell}$<0), resulting from favorable interactions between hydrophilic groups and water molecules, and a mediating loss of polymer chain conformation entropy ($\Delta S_{swell}$<0) during the same swelling. This behavior is well described by Flory-Rehner theory. In our case, the hydrophilic PEG blocks were hydrated by water molecules, leading to mass gain and volumetric expansion. However, complete dissolution was prevented by the presence of hydrophobic POSS-rich domains, serving as physical cros slinks. FIG. 2(A) shows the swelling behavior of a cast film containing AgNO$_3$ through photographs before (i) and after (ii) swelling to equilibrium.

Surprisingly, electro-spun nano-fibrous mats do not expand during immersion in water, but instead shrink slightly, as shown in FIG. 2(B). This behavior is unprecedented in the literature. The slight contraction may be due to orientation relaxation upon swelling, axially contracting the fibers to the point of inter-fiber impingement. Subsequent swelling may be suppressed by "memory" of the nanofibrous internal microstructure that may feature highly anisotropic swelling characteristics (greater extent in radial direction than in axial direction), coupled with the inter-fiber impingement constraint. This poorly understood phenomenon deserves future intensive study; however, it remains quite reproducible that mass gain during dimensional contraction is reproducibly observed in such specimens, as summarized in Table 2.

TABLE 2

Swelling behavior of POSS-PEG TPUs

|  | Cast Film w/ 1.0 wt % AgNO$_3$ | Electro-spun Mat w/ 1.0 wt % AgNO$_3$ |
| --- | --- | --- |
| Water uptake (%) | 474 ± 25 | 517 ± 36 |
| Swelling ratio (%) | 66.1 ± 3.3 | −17.4 ± 1.0 |

The internal microstructure of the resulting hydrogels was examined using a freeze-drying sample preparation (preserving internal structure) and SEM inspection of fracture surfaces. Porous microstructures of hydrogels were observed for the cast film hydrogel sample, featuring pores with varying size from 20 to 50 µm in diameter (FIG. 8). In contrast, the nano-fibrous web hydrogels were not porous, but instead featured compacted internal structures believed to be a reflection of macroscopic shrinkage behavior in water (Supplementary Figure S2). The same compacted microstructure was also observed in the hydrogels with high hydrophobic POSS loading. In next section, we will discuss—in part—the influence of this unique swelling behavior and internal structure on the corresponding antimicrobial effects and durability.

Antimicrobial Activity

The nanostructured hydrogel mats with and without AgNO$_3$ were sterilized by UV illumination under a universal UV light source ($\lambda$.=254 nm, 42 W) in a Biological Safety Cabinet prior to any antimicrobial testing, in order to avoid the possible pre-test contamination. It was found that a 15 min UV-exposure was sufficient to sterilize the hydrogels, since no microbes were detected from the treated samples after culturing in LB medium for one day (no colony-forming units were seen). Such UV-sterilized hydrogels were then challenged with *E. coli* RP437 pRSH103 in LB medium for varying periods of time (up to 14 d). The antimicrobial activities of the POSS-PEG TPUs hydrogels with and without AgNO$_3$ were evaluated by analyzing *E. coli* biofilm formation on these materials using both SEM and fluorescence microscopy.

Figure 3:
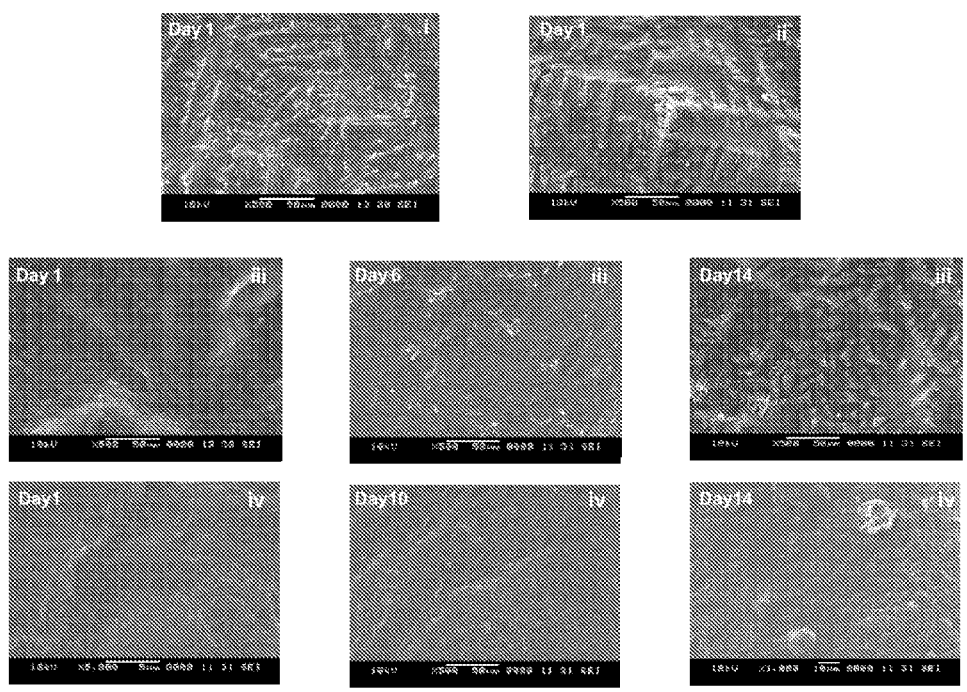
FIG. 3 is a series of SEM micrographs to assess antimicrobial efficacy of POSS-PEG TPU hydrogels samples cultured in *E. coli* containing LB medium at 37° C. for various periods of time: (i) cast film without $AgNO_3$; (ii) electrospun mat without $AgNO_3$; (iii) cast film with 1.0 wt % $AgNO_3$; (iv) electrospun mat with 1.0 wt-% $AgNO_3$.

SEM observations evidenced that the AgNO$_3$ incorporation rendered the hydrogel samples to feature the antimicrobial effect. FIG. 3 shows SEM images of different POSS-PEG TPU hydrogels samples exposed to *E. coli* in LB medium at 37° C. for various lengths of time. Neither the cast film nor the electrospun fibrous web control (i.e., without silver nitrate) exhibited an antimicrobial effect. To the contrary, FIG. 3 (i: Day 1) and (ii: Day 1) shows that *E. coli* cell clusters are apparent on both samples after incubation for only one day. In comparison, *E. coli* cells are almost completely absent on the entire surface of the cast film incorporating 1.0 wt-% AgNO$_3$ loading after incubation for one day (FIG. 3 (iii: Day 1)), but not for later time observations of six and fourteen days, for which *E. coli* cell clusters are evident. Similar results were also observed for the electro-spun nanofibrous mat incorporating 1.0 wt-% AgNO$_3$ (FIG. 3 (iv: Day 1)), though with attractive prolonged antimicrobial activity evidenced by the lack of *E. coli* cell clusters even after fourteen days. These data are consistent with previous reports that incorporation of AgNO$_3$ in hydrogels is effective in preventing microbial biofilm formation.

Uniquely, the nanofibrous silver-containing mat showed significantly prolonged effects when compared to the cast film also containing silver. After incubation for 6 days, a few *E. coli* cells can be observed on the surface of the cast film initially incorporating 1.0 wt-% AgNO$_3$, as shown in FIG. 3. (iii: Day 6). After 14 days, however, *E. coli* biofilms spread and covered the entire cast film (FIG. 3. (iii: Day 14)), which is similar to the one without AgNO$_3$ incorporation (FIG. 3 (i: Day 1)). This observation indicates that after 14 days of incubation in LB medium, the cast film loses its antimicrobial activity, possibly because the incorporated Ag$^+$ ions have been totally released out of the cast film. In contrast, we cannot see any *E. coli* cells on the surface of electrospun nanofibrous mat with 1.0 wt-% AgNO$_3$ loading after 10 days of incubation (FIG. 3. (iv: Day 10)). Even after incubation for 14 days, the surface of electrospun nanofibrous mats incorporating 1.0 wt-% AgNO$_3$ was still barely colonized (FIG. 3 (iv: Day 14)). These observations indicate that the antimicrobial activity of electrospun nanofibrous mat has a much longer duration than a comparable cast film with the same AgNO$_3$ loading.

Figure 4:
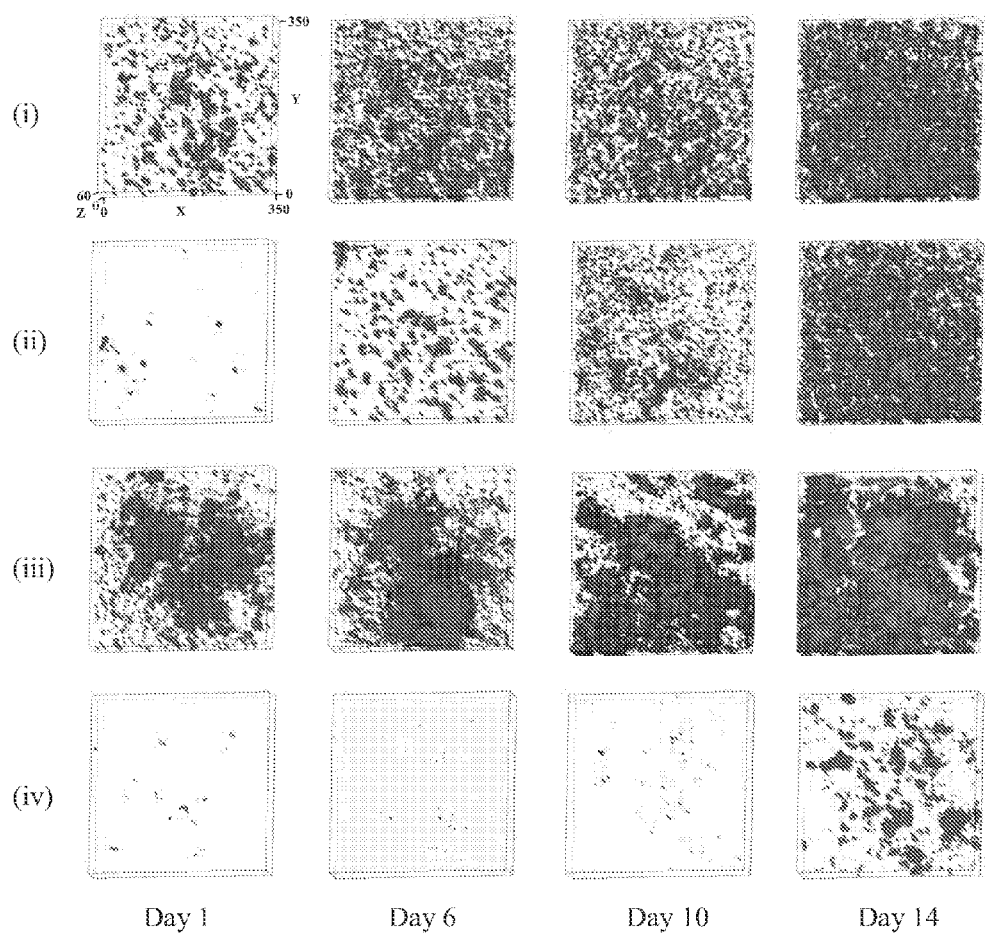
FIG. 4 is a series of representative 3-D microscope images of *E. coli* biofilms formed on various hydrogel samples: (i) cast film without silver, (ii) cast film with silver, (iii) nanofiber web without silver (iv) nanofiber web with silver.

The fluorescence microscopy investigations confirmed our observations in SEM further. FIG. 4 (*i-iv*) shows the fluorescence microscopy images of *E. coli* biofilms on different hydrogels. Both the cast film and the electrospun nanofibrous mat with 1.0 wt-% AgNO$_3$ incorporation exhibited significant antimicrobial effects. After incubation for one day, only several attached cells can be seen. In contrast, the counterparts without AgNO$_3$ loading were extensively covered by *E. coli* biofilms. The coverage of bacteria on electrospun nano-fibrous hydrogel (FIG. 4 (iii: Day-1)) is more extensive than that of the cast film (FIG. 4 (i: Day-1)). This difference may be attributed to the higher surface area of the nanofibrous hydrogel that, without silver elution, allows for *E. coli* adherance. For the cast film with 1.0 wt-% AgNO$_3$ loading, *E. coli* cell clusters can be observed after incubation for 6 days and the coverage increases with incubation time. In comparison, the electrospun nano-fibrous mat incorporating 1.0 wt-% AgNO$_3$ shows a much longer duration of antimicrobial effect. Even after incubation for 10 days, we observed only a few sparsely distributed *E. coli* cell clusters, almost indistinguishable from the surface incubated for just one day. When incubated for 14 days, the surface was still only sparsely covered with bacteria. The data obtained by fluorescence microscopy analysis are consistent with the results from SEM.

Figure 5:
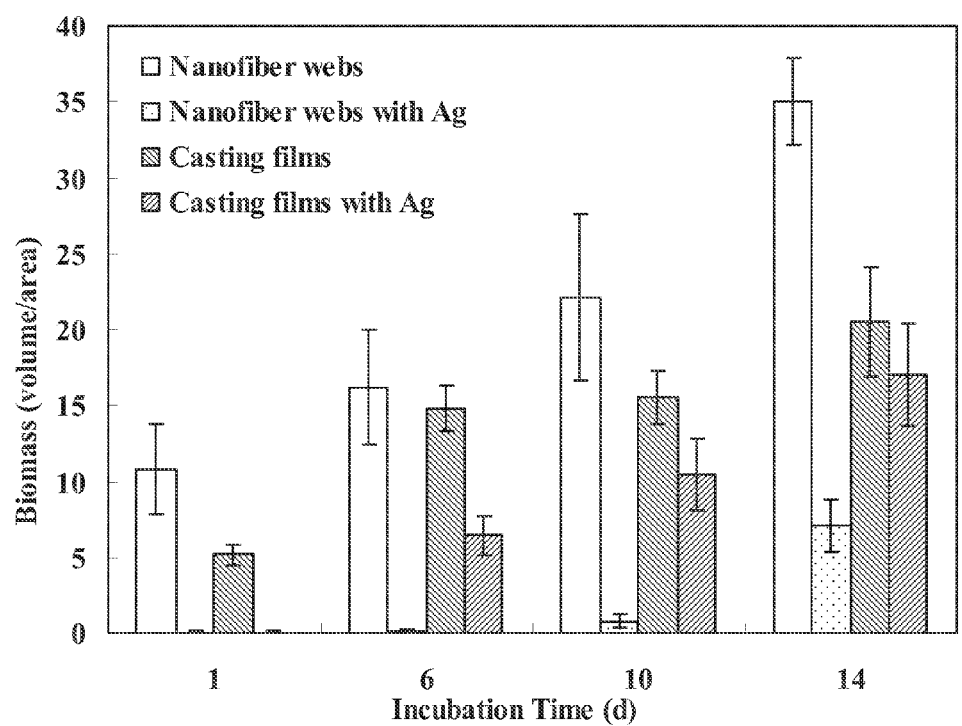
FIG. 5 is a graph of the total biomass (volume/area: $\mu m^3/\mu m^2$) of *E. coli* biofilms with different incubation time (1, 6, 10, and 14 days) is summarized in (b); where the data were calculated by the COMSTAT software written on the Matlab platform.

To quantitatively compare the antimicrobial activities of different samples, the fluorescence microscopy images were analyzed for biofilm biomass using COMSTAT software, the results of which are shown in FIG. 5. The hydrogel samples with AgNO$_3$ had significantly less biofilm biomass than the ones without AgNO$_3$. After 14 days of incubation in LB medium containing *E. coli* PR437/pRSH103, the biomass formed on non-silver samples was substantial: 20.5±3.6 µm$^3$/µm$^2$ for neat cast film and 35.0±2.9 µm$^3$/µm$^2$ for electro-spun nanofibrous web. As for the samples incorporating 1.0 wt-% AgNO$_3$, both cast film and electro-spun nano-fibrous web initially killed nearly all bacteria and showed almost no biofilm. After 6 days of incubation, the silver containing cast film lost its antimicrobial effect and 6.4±1.4 µm$^3$/µm$^2$ of biomass formed. In the following days, the biomass increased at a rate of 1.3 µm$^3$/µm$^2$ per day, on average, reaching 17±3.3 µm$^3$/µm$^2$ after 14 days of incubation. For the electrospun nanofibrous web incorporating 1.0 wt-% AgNO$_3$, its biomass value remained almost zero until after 14 days of incubation, when it reached 7.1±1.8 µm$^3$/µm$^2$, indicating that the sample began to lose its antimicrobial effect at that time.

It is known that when in contact with blood, a biomaterial surface can be quickly covered by host proteins. Thus, the ability to release antimicrobials may have advantages over covalent modifications. Consistently, the nanofibers used in this study were found to inhibit biofilm formation for 14 days in the presence of sticky polysaccharides secreted by *E. coli*.

This finding suggests that the nanofibers with prolonged silver release may maintain the antimicrobial activity when exposed to sticky proteins. To determine whether the antimicrobial activities were restricted to inhibition of biofilms on the surfaces or also existed against planktonic cells due to the elution of ionic silver, the $OD_{600}$ of planktonic cultures after 24 h incubation with nanofibers in the presence and absence of silver were also tested. No apparent inhibition of planktonic growth was observed (data not shown). Therefore, the anti-biofilm activities of silver-loaded nanofibers should be surface specific. Under the same $AgNO_3$ loading, electrospun nanofibrous hydrogel mats enable a prolonged antimicrobial effect. This unique property may be due mainly to its compacted internal microstructure that may control the rate of silver ion elution, and the silver ion availability at the hydrogel surface. Further research could quantitatively examine such kinetics and relate it to the nanofibrous hydrogel microstructure. If the subject materials were to be used for wound dressings, the lack of swelling would be an attractive property in that it would minimize "lateral wicking", an undesirable property of many wound dressings, and consequently prevent (or reduce) associated excoriation and maceration of the skin at the edges of heavily exuding wounds. Thus, there is a utility of the antimicrobial nanofibrous hydrogels in such applications as bandages, wound dressings, and reconstructive oral and bone surgery.

The present invention involves new electrospun nano-fibrous webs featuring excellent antimicrobial properties. Specifically, PEG-based multi-block thermoplastic polyurethanes (TPUs) incorporating POSS moieties were co-dissolved with silver nitrate($AgNO_3$) and subsequently electrospun to yield durable hydrogel webs capable of controlled silver ion release for effective antimicrobial behavior, which was analyzed quantitatively. Due to significant thermodynamic incompatibility between POSS moieties and ethylene oxide units, POSS nanocrystals, resulting from microphase separation, serve as physical crosslinking points within an inorganic-organic hybrid network, in turn affording novel hybrid 16 organic-inorganic hydrogels in the water-swollen state. In contrast to conventional hydrogels, the electrospun nanofibrous scaffolds of the present invention hydrate with macroscopic volume shrinkage during significant water uptake. The resulting organic-inorganic hybrid hydrogel scaffolds not only feature compact internal microstructures, but also display a desirable prolonged antimicrobial effect. For instance, antimicrobial tests demonstrated that the electrospun nano-fibrous webs (fiber diameter=150±2 nm) prepared from TPUs incorporating 1.0 wt-% $AgNO_3$ loading can effectively suppress *E. coli* biofilm formation for 14 days, which is much longer than its cast (non-porous) film counterpart that only suppressed *E. coli* biofilm formation for 1 day. This arrested swelling may control the rate of $Ag^+$ release from the electro-spun hydrogel scaffold and $Ag^+$ availability at the hydrogel surface. The hydrogels of the present invention are thus useful materials for controlling biofilm infections, with promising applications in wound dressings and reconstructive oral and bone surgery.

What is claimed is:

1. A nanofiber hydrogel, comprising:
   a fibrous web comprised of a plurality of fibers formed from a thermoplastic polyurethane comprising a polyhedral oligosilsesquioxane, polyethylene glycol, and a silver compound, wherein said fibers have a diameter of between 100 and 250 nanometers.

2. The nanofiber hydrogel of claim 1, wherein said thermoplastic polyurethane further comprises a diisocyanate.

3. The nanofiber hydrogel of claim 2, wherein said diisocyanate is lysine methyl-ester diisocyanate.

4. The nanofiber hydrogel of claim 3, wherein said polyhedral oligosilsesquioxane and said diisocyanate form a hard segment that alternates with a soft segment comprising polyethylene glycol.

5. The nanofiber hydrogel of claim 1, wherein said silver compound is silver nitrate.

6. The nanofiber hydrogel of claim 1, wherein said silver compound is present at a concentration of approximately 1 wt-% relative to said thermoplastic polyurethane.

7. The nanofiber hydrogel of claim 1, wherein said hydrogel is an antimicrobial.

8. A hydrogel wound dressing, comprising:
   a nanofiber hydrogel comprising a fibrous web of a plurality of fibers, each of which has a diameter of between 100 and 250 nanometers and is comprised of a thermoplastic polyurethane including a polyhedral oligosilsesquioxane and polyethylene glycol; and
   a silver compound.

9. The hydrogel wound dressing of claim 8, wherein said nanofiber hydrogel comprises electrospun fibers.

10. The hydrogel wound dressing of claim 8, wherein said wound dressing releases silver ions in a time-release manner.

11. The hydrogel wound dressing of claim 10, wherein said silver ions are released in an amount sufficient to kill one or more microorganisms.

12. The hydrogel wound dressing of claim 8, wherein said silver compound is silver nitrate.

13. A method of preventing the growth of microorganisms on a surface, the method comprising the step of placing said surface in communication with a nanofiber hydrogel, wherein the nanofiber hydrogel comprises a fibrous web comprised of a plurality of fibers formed from a thermoplastic polyurethane comprising a polyhedral oligosesquioxane, polyethylene glycol, and a silver compound, wherein said fibers have a diameter of between 100 and 250 nanometers.

14. The method of claim 13, wherein said surface is a wound.

15. The method of claim 13, wherein said surface is inside a human body.

16. The method of claim 13, further comprising the step of sterilizing said nanofiber hydrogel before placing it in communication with said surface.

17. The method of claim 16, wherein the step of sterilizing said nanofiber hydrogel comprises UV sterilization.

18. The method of claim 13, wherein said nanofiber hydrogel is a web of electrospun fibers comprising said thermoplastic polyurethane.

19. The method of claim 13, wherein said silver compound is silver nitrate.

20. The method of claim 13, wherein said nanofiber hydrogel releases silver ions in a time-release manner.

* * * * *